United States Patent [19]

Suzuki et al.

[11] Patent Number: 4,500,639

[45] Date of Patent: Feb. 19, 1985

[54] CULTURING BORDETELLA IN MEDIA CONTAINING ETHERIFIED CYCLODEXTRIN

[75] Inventors: Yoji Suzuki; Atsushi Imaizumi; Hisao Yamaguchi; Masaharu Kanesaki, all of Hino; Shoji Ono, Kodaira, all of Japan

[73] Assignee: Teijin Limited, Tokyo, Japan

[21] Appl. No.: 427,039

[22] Filed: Sep. 29, 1982

[30] Foreign Application Priority Data

Oct. 15, 1981 [JP] Japan .............................. 56-163477
Oct. 15, 1981 [JP] Japan .............................. 56-163478

[51] Int. Cl.³ .................. C12N 1/38; C12P 21/00; C12Q 1/04; C12R 1/01
[52] U.S. Cl. .................................. 435/244; 435/34; 435/68; 435/243; 435/822
[58] Field of Search ................ 435/253, 244, 68, 34, 435/822

[56] References Cited

U.S. PATENT DOCUMENTS

| | | | |
|---|---|---|---|
| 2,240,969 | 8/1937 | Voigt | 435/253 |
| 3,577,319 | 5/1971 | Nielsen et al. | 435/253 |
| 3,852,423 | 12/1974 | Nakase et al. | 435/822 |
| 4,317,881 | 5/1982 | Yagi et al. | 435/97 |

FOREIGN PATENT DOCUMENTS 0012718 6/1980 European Pat. Off. .............. 253/

OTHER PUBLICATIONS

Radley, J. A., Starch and its Derivatives 4th Edition, 1968, Distribution in USA by Barnes and Noble, Inc., pp. 290-301.
Imaizumi et al., Infection and Immunity, Sep., 1983, pp. 1138-1143.
Rowatt, Journal of General Microbiology, vol. 17, pp. 297-326, (1957).
Stainer et al., Journal of General Microbiology, (1971), vol. 63, pp. 211-220.
Tilden et al., Journal of the American Chemical Society, vol. 64, 1942, p. 1432.
Yojima et al., Journal of Biochemistry, (1978), vol. 83, pp. 305-312.

*Primary Examiner*—Sidney Marantz
*Assistant Examiner*—William J. Herald
*Attorney, Agent, or Firm*—Sughrue, Mion, Zinn, Macpeak & Seas

[57] ABSTRACT

A method of culturing microbes which belong to the genus Bordetella characterized by adding cyclodextrin or its derivative to the culture medium used for cultivating microbes belonging to the genus Bordetella and a culture medium therefor.

7 Claims, 4 Drawing Figures

CULTURING BORDETELLA IN MEDIA CONTAINING ETHERIFIED CYCLODEXTRIN

BACKGROUND OF THE INVENTION

This invention relates to a method of culturing microbes which belong to the genus Bordetella and a culture medium to be used in the culture and a method for preparing biologically active substances using said culture medium.

The microbes of the genus Bordetella include *Bordetella pertussis, Bordetella parapertussis, Bordetella bronchiseptica*, etc., of which *Bordetella pertussis* is especially known as a pathogenic bacterium which attacks the tracheas, bronchia, and bronchiolus of an infected patient to cause whooping cough and aflicts the patient with a paroxysmal cough for a long duration of several weeks. A means of prompt and accurate detection of the *Bordetella pertussis*, etc. is therefore earnestly desired from a clinical viewpoint. Such a desired method of cultivation or a culture medium should promote the culture of clinically obtained and separated causative bacteria. Also, such a method of cultivation or the culture medium should promote the growth of *Bordetella pertussis* for the efficient production of pertussis vaccine (killed whole cell vaccine or component vaccine) which is used for the prevention of whooping cough. Medically effective biologically active substances such as islet activating protein (hereinafter referred to as IAP) from which a remedy and prevention of diabetes is expected to be developed, leukocytosis promoting factor-hemagglutinin (hereinafter referred to as LPF-HA) and filamentous-hemagglutinin (hereinafter referred to as F-HA) which are attracting medical attention as acellular pertussis vaccine component, etc. are obtained from the cultured substance (consisting of the culture medium and cultured bacteria) of *Bordetella pertussis* Phase I. An effective method for culturing *Bordetella pertussis* is sought in order to achieve an increased productivity in the preparation of the above-described biologically active substances.

As for the culture medium for the growth of bacteria belonging to the genus Bordetella, especially *Bordetella pertussis* phase I, there are well-known culture media, in which active carbon and starch or ion-exchange resin are involved, originated by Cohen et al. (American Journal of Public Health, vol 36, pp. 371-376, 1946) and Sutherland et al. (Journal of Pathology and Bacteriology, vol. 82, pp. 431-438, 1961). However, charcol and ion-exchange resin which can't permit uniformity in the culture medium restrict the work of monitoring the proliferation of bacteria and also the effect on eliminating the preventive factors such as fatty acid, etc. which arrest the growth of bacteria is not always selective because of their unspecific absorbability. Furthermore, the effect of starch upon the growth of bacteria is not sufficient. It has therefore been desired to develop a new culture medium in which the above-mentioned disadvantages are all corrected. In order to clinically isolate *Bordetella pertussis* as exclusive single colonies, it is necessary to make airborne droplets emitted from an infected patient directly contact a solid agar culture medium such as Bordet-Gengou medium (hereinafter referred to as BG medium). However, a culture medium of this kind requires fresh blood as an essential component, therefore, its preservability is very low, and possesses a defect of being not stable of colony-forming ability. From the points of view mentioned above, the development of an culture medium for clinical isolation having a certain clearly defined chemical composition and high preservability has long been hoped for.

In recent years, a synthetic culture medium has been developed by Stainer and Scholte for mass cultivation of *Bordetella pertussis* (Journal of General Microbiology, vol. 63, pp. 211-220, 1971). Since Stainer-Scholte medium (hereinafter referred to as SS medium) does not contain such additives as blood and polypeptone arising from natural sources that are inducible of qualitative difference between lots, it is possible to achieve a strict control of the medium composition and carry out the cultivation of bacteria without bringing about changes in their nature. Besides, it has another merit of being capable of keeping away other unnecessary reactogenic proteins in the culture system during the processes of separating and purifying biologically active substances such as before-mentioned IAP and LPF-HA. Because of the characteristics mentioned above, SS medium has recently come to be widely used in commerically preparing pertussis vaccine and biologic active substances from *Bordetella pertussis*; however, it has the disadvantage of not promissing enough production of LPF-HA in the liquid culture under shaking or static conditions and also not promissing stable growth of bacteria when the inoculation is conducted at seed concentration of $10^7$ cells/ml or less. Solid SS agar medium (hereinafter referred to as SSA medium) obtained by solidifying SS medium by use of agar amounting to 1 to 2% of the whole has an evident disadvantage of not being capable of forming colonies when inoculating at a low concentration of $10^7$ cells/ml or less.

SUMMARY OF THE INVENTION

A primary object of the present invention is to provide a method of culturing microbes which belong to the genus Bordetella with stability and efficiency and a method of their isolation.

Another object of the present invention is to provide a culture medium to be used in culturing said microbes.

Other object of the present invention is to provide a method of preparing a biologically active substance from the microbes belonging to the genus Bordetella cultured in said culture medium.

A general object of the present invention is achieved by a method of culturing microbes belonging to the genus Bordetella characterised by the addition of cyclodextrin or its derivative to the culture medium at the time of culturing the microbes belonging to the genus Bordetella, a culture medium which is made to contain cyclodextrin or its derivative, and a method of preparing a biologically active substances comprising culturing microbes belonging to the genus Bordetella on a culture medium containing cyclodextrin or its derivative and obtaining the biologically active substances from the cultured substance (consisting of the culture medium and cultured microbes).

DESCRIPTION OF THE PREFERRED EMBODIMENT

Figure 1:
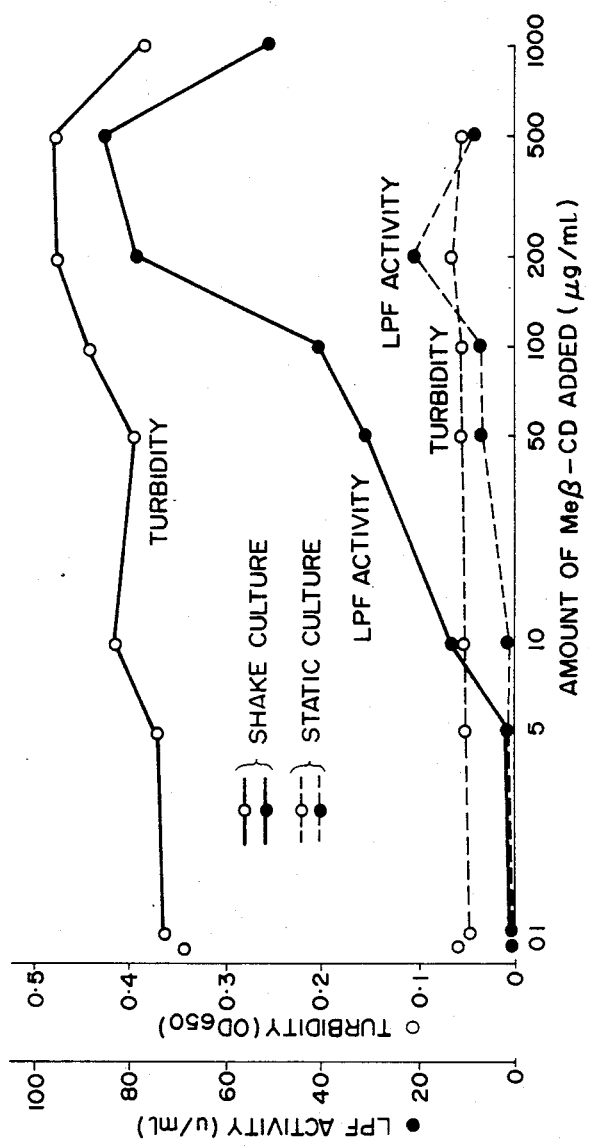
FIG. 1 is a graph to show the relationship of the amount of heptakis(2,6-O-dimethyl)$\beta$-cyclodextrin (Me$\beta$-CD) added to the medium for the culture of *Bordetella pertussis* phase I versus turbidity of the culture medium and the amount of produced LPF-HA (LPF activity).

The microbes belonging to the genus Bordetella referred to in the present invention are *Bordetella pertussis, Bordetella parapertussis,* and *Bordetella bronchiseptica.* The one which is desirably used in the present invention is *Bordetella pertussis* and *Bordetella pertussis* phase I is especially desirable. A scientific description of the bacteriological nature and conditions of cultivation relative to the microbes belonging to the genus Bordtella is found in Bergy's Manual of Determinative Bacteriology, 8th edition, 1974, published by The Williams & Willkins Co., Journal of Exp. Med., vo. 129, pp. 523-550, 1969, and Practical Manual of Bacteriology, 3rd edition, p. 80, 1972, published by Maruzen, Tokyo, and it is already a matter of public knowledge.

Cyclodextrin is a crown-like molecule obtained by letting a cyclodextrin-transglycosylose produced by microorganism such as *Bacillus macerans* act on starch or a hydrolized product of starch with 6 to 10 D-glycopyranose groups linked cyclically with each other by α-1,4 glycoside bonds. Its main varieties are α-, β-, and γ-cyclodextrins comprising 6, 7, and 8 D-glycopyranose groups respectively. What is referred to as cyclodextrin in the present invention means the above-mentioned α-, β-, γ-cyclodextrin or a mixture thereof.

As a molecule of cyclodextrin has many primary and secondary hydroxyl groups, various kinds of derivatives are obtained from cyclodextrin by subjecting it to a reaction which is generally used for monosaccharide. Derivatives of cyclodextrin referred to in the present invention indicate those derivatives obtained according to such method and, among them, aminated derivatives such as aminocyclodextrin and aminodeoxycyclodextrin, esterified derivatives such as acetylcyclodextrin and nitroxycyclodextrin, and etherified derivatives (etherified cyclodextrins) such as methylcyclodextrin, ethylcyclodextrin, propylcyclodextrin and carboxymethylcyclodextrin are known. In the present invention, the use of etherified cyclodextrins are desirable, of which methyldextrins such as hexakis(2,6-O-dimethyl)α-cyclodextrin and heptakis(2,6-O-dimethyl)β-cyclodextrin are especially desirable.

A culture medium in the present invention includes such known liquid media as nutrient bouillon and peptone water and solid media prepared by adding agar, gelatin, albumin, blood serum, etc.; however, SS medium (or SSB medium) and SSA medium which is a solid medium obtained by adding 1 to 2% (W/v) of agar to SS medium are desirable.

SS medium is usually prepared by adding a supplemental solution, which is obtained by sterilization by use of a millipore filter (0.45μ) from an aqueous solution containing 4, 1, 2, 0.4 and 10 g respectively of l-cystine, ferrous sulfate, ascorbic acid, niacin, and glutathione of reduced type per liter of solution at an amount of 1.0% (v/v) to the basal medium, which is obtained by preparing an aqueous solution containing 10.7, 0.24, 2.5, 0.5, 0.2, 0.1, 0.02, and 1.525 g respectively of sodium glutamate, l-proline, sodium chloride, potassium dihydrogenphosphate, potassium chloride, magnesium chloride, calcium chloride, and trishydroxymethylaminomethane per liter of solution, adjusting the pH value of thus prepared solution to 7.6, and sterilizing the solution in an autoclave at 121° C. for 15 minutes.

In the present invention, a variant of said SS medium obtained by adding 0.5 to 10 g/l of casamino acid to its basal medium and also by modifying the contents of ascorbic acid and glutathione of reduced type in supplemental solution to 10 to 40 g/l and 10 to 100 g/l respectively is especially preferable.

Also in the present invention, the amount of cyclodextrin or its derivative to be admixed with said culture medium varies depending upon the count of microbes to be inoculated and 200 to 5,000 μg/ml, more preferably 500 to 5,000 μg/ml, for the bacterial concentration of $10^2$ to $10^3$ cells/ml and 1 to 5,000 μg/ml, more preferably 50 to 2,000 μg/ml, for the bacterial concentration of $10^7$ to $10^9$ cells/ml are proper. Since thus prepared culture medium containing cyclodextrin or its derivative is assured of stable and effective growth of microbes, it can be used for the cultivation and detection of *Bordetella pertussis* in clinical field. This culture medium is also a very advantageous medium for producing biologically active substances such as IAP which is expected to have diabetotherapeutic efficacy, LPF-HA and F-HA which are expected to be used as pertussis vaccine components, and for preparing bacterial vaccine.

The method and conditions for cultivating microbes belonging to the genus Bordetella by use of such culture medium are in no way specifically limited and any known conventional methods and conditions can be adopted; however, shake culturing is preferable to stationary culturing and it is desirable to carry out the cultivation at 30° to 38° C. for 10 to 100 hours.

No limit is specifically placed upon the method and means of collecting the produced biologically active substances from the cultured substance (culture medium and cultured bacteria) and known methods and means can be applied. For instance, LPF-HA can be obtained as follows. *Bordetella pertussis* phase I (ex. *Bordetella pertussis* strain Tohama) is grown at 35° C. on SS medium containing methyl β-cyclodextrin for 48 hours. The supernatant (pH 8.3) obtained by centrifuging the culture fluid is applied to a column of hydroxylapatite equilibrated with a 0.01M phosphate buffer (pH 8.0). The solution passing through the column is adjusted to pH 6.0 and then is applied a column of hydroxylapatite equilibrated with a 0.01M phosphate buffer (pH 6.0) and the bounded protein is then eluted with a 0.1M phosphate buffer (pH 7.0) containing 0.5M sodium chloride. Thus the eluate is applied to the affinity column using haptoglobin-Sepharose 4B and LPF-HA is then eluted with a 0.1M phosphate buffer (pH 7.0) containing 0.5M sodium chloride and 3M potassium thiocyanate.

F-HA is obtained by eluting the bounded protein in the column of hydroxylapatite (pH 8.0) with a 0.1M phosphate buffer (pH 7.0) containing 0.5M sodium chloride and by purifying the eluate with the affinity column chromatography using haptoglobulin-Sepharose 4B.

The following examples illustrate the present invention:

EXAMPLE 1

Lyophilized cells of *Bordetella pertussis* Tohama phase I were suspended in a 1% casamino acid solution and then grown on BG medium containing 20% defibrinated horse blood at 35° C. for 3 days. One loopful of growing cells were refreshed on BG medium for 24 hours, and suspended in SS medium to obtain suspension having a concentration of $5 \times 10^3$ cells/ml.

Solid SSA medium of 1.2% agar density containing cyclodextrin or its derivative to a prescribed final concentration (μg/ml) was spread on the plates at cell counts of $10^3$ cells per plate.

The results of cell growth (the number of colony-forming units) after the 4-day incubation at 35° C. are shown in Table 1.

TABLE 1

| | Amount of cyclodextrin or its derivative added (μg/ml) | | | | | |
|---|---|---|---|---|---|---|
| | 0 | 100 | 200 | 500 | 1000 | 2500 | 5000 |
| α-CD | − | − | − | − | ± | + | − |
| Meα-CD | − | − | ± | + | ++ | + | − |
| Etα-CD | − | − | ± | ± | + | + | − |
| β-CD | − | − | − | − | ± | + | ± |
| Meβ-CD | − | − | + | ++ | ++ | + | ± |
| Etβ-CD | − | − | ± | ± | + | + | ± |
| γ-CD | − | − | − | − | ± | ± | + |
| Meγ-CD | − | − | − | − | ± | + | + |

Note:
− Less than 10 colonies
± 10–100 colonies
+ 100–500 colonies
++ 500–1000 colonies Etherified cyclodextrin which was used in the experiment was prepared according to the method proposed by H. Schlenk et al. (see Abstr. Pap. Amer. Chem. Soc., 149, 11c, 1965).

Hereinafter α-cyclodextrin is referred to as α-CD, its methylated derivative, hexakis(2,6-O-dimethyl)α-cyclodextrin, as Meα-CD, ethylated derivative as Etα-CD, β-cyclodextrin as β-CD, its methylated derivative, heptakis(2,6-O-dimethyl)β-cyclodextrin, as Meβ-CD, ethylated derivative as Etβ-CD, γ-cyclodextrin as γ-CD, and its methylated derivative as Meγ-CD respectively.

Table 1 clearly shows that the addition of cyclodextrin or its derivative to the culture medium promotes the growth of *Bordetella pertussis*, that α-CD, β-CD, and γ-CD enhance their effect when they are methylated or ethylated, that β-derivatives are superior to α-derivatives, and that γ-derivative is somewhat inferior to α-derivatives and β-derivatives in effectiveness.

EXAMPLE 2

A suspension for inoculation obtained according to Example 1 was inoculated on 1.0 ml of SS medium (SSB medium, liquid) containing Meβ-CD of a prescribed concentration at cell counts of $10^6$ cells and was allowed to grow at 35° C. in a Monod's L-test tube with shaking. The turbidity (OD 650 mμ) of the resulting medium changed as time passed as shown in Table 2.

TABLE 2

| Amount of Meβ-CD added (μg/ml) | Turbidity of medium (OD 650 mμ) | | | |
|---|---|---|---|---|
| | 17 hrs | 25 hrs | 44 hrs | 50 hrs |
| 0 | 0.005 | 0.017 | 0.280 | 0.490 |
| 1 | 0.010 | 0.023 | 0.340 | 0.540 |
| 5 | 0.011 | 0.024 | 0.330 | 0.540 |
| 10 | 0.015 | 0.033 | 0.370 | 0.500 |
| 50 | 0.015 | 0.044 | 0.430 | 0.675 |
| 100 | 0.015 | 0.037 | 0.430 | 0.695 |
| 500 | 0.016 | 0.050 | 0.540 | 0.747 |
| 1000 | 0.007 | 0.011 | 0.300 | 0.485 |

It may be found from Table 2 that when Meβ-CD is added to the medium in the range of 1 to 500 μg/ml, the turbidity of the medium increases as the amount of Meβ-CD increases which indicates that the growth of microbes is promoted.

EXAMPLE 3

Improved SSA media were prepared by increasing the concentration of glutathione of reduced type 1.5 times ordinary SSA medium and also fixing the concentrations of casamino acids at 0, 500, 1000, 2500, 5000, and 10000 μg/ml and the concentrations of Meβ-CD at 0, 50, 100, 250, 500, and 1000 μg/ml respectively. About 100 cells of *Bordetella pertussis* Tohama phase I were spread on each plate of medium and grown at 35° C. for 3 days. The number of formed colonies was compared with the number of colonies formed on BG medium under the same conditions in Table 3. It is clear from the table that the addition of Meβ-CD in the range of 500 to 1000 μg/ml makes the number of formed colonies equal to that obtained with BG medium. The addition of casamino acids in the range of 500 to 5000 μg/ml makes the size of the formed colonies larger and obvious.

TABLE 3

| casamino Acids (μg/ml) | Numbers of colonies/plate Meβ-CD (μg/ml) | | | | | |
|---|---|---|---|---|---|---|
| | 0 | 50 | 100 | 250 | 500 | 1000 |
| 0 | 0 | 0 | 0 | 0 | 116* | 89* |
| 500 | 0 | 0 | 1 | 64 | 123 | 109 |
| 1000 | 0 | 0 | 0 | 0 | 98 | 112 |
| 2500 | 0 | 0 | 0 | 0 | 99 | 121 |
| 5000 | 0 | 0 | 0 | 0 | 102 | 137 |
| 10000 | 0 | 0 | 0 | 0 | 0 | 74 |

Bordet-Gengon control = 104 ± 16 colonies/plate (N = 5)
*Colonies were somewhat small.

EXAMPLE 4

Lyophilized cells of *Bordetella pertussis* Tohama phase I were suspended in a 1% casamino acid solution and then grown on BG medium containing 20% defibrillated horse blood at 35° C. for 3 days. One loopful of the cells were refreshed on BG medium for 24 hours, and suspended in SS medium to obtain an inoculum suspension. This suspension was suspended in SS medium containing Meβ-CD of prescribed concentration in such a way as to make cell counts of $10^7$ cells/ml and cultivated at 35° C. for 18 hours under static or shaking conditions.

After the cultivation was over, the turbidity (OD 650 mμ) of the liquid medium was measured and then LPF-HA was produced according to the method mentioned below and its activity was determined. The supernatant (pH 8.6) obtained by centrifuging. The culture fluid was applied to a column of hydroxylapatite equilibrated with a 0.01M phosphate buffer (pH 8.0). The solution passing through the column was adjusted to pH 6.0 and then was applied to a column of hydroxylapatite equilibrated with a 0.01M phosphate buffer (pH 6.0) and the bounded protein was then eluted with a 0.01M phosphate buffer (pH 7.0) containing 0.5M sodium chloride. Thus the eluate was applied to an affinity column using haptoglobin-Sepharose 4B and LPF-HA was then eluted by use of 0.1M phosphate buffer (pH 7) containing 0.5M sodium chloride and 3M potassium thiocyanate.

LPF activity was determined according to the Enzyme-Linked Immuno Sorbent Assay method (ELISA method proposed by Sato et al. at the 28th Symposium on Toxin held on July 23 to 24, 1981, at Hachimantaira, Iwate Prefecture, Japan: Abstract of lectures, pp. 141 to 144 and also published in Jap. J. Med. Sci. Biol., Vol 35, pp. 135 to 136) and the activity units (u) of LPF-HA were expressed by the dilution multiple of the respective samples based on 0.1 per unit volume (ml) at OD 400 m$\mu$.

The result is shown in FIG. 1, from which it is clearly seen that Me$\beta$-CD remarkably enhanced the production of LPF-HF per cell count especially under the conditions accompanied by reciprocal shaking.

Also the use of Me$\alpha$-CD accomplished practically similar encouraging result.

EXAMPLE 5

An inoculum suspension obtained according to Example 4 was suspended in 150 ml of SS medium (liquid medium) containing Me$\beta$-CD at an amount of 500 $\mu$g/ml in such a way as to obtain cell concentration of $3.3 \times 10^8$ cells/ml and cultivated at 35° C. for periods of respectively predetermined time with shaking. The relationship between the culture time versus turbidity of the medium and amount of produced LPF-HA (LPF activity) is shown in FIG. 2.

Incidentally, LPF activity was determined according to Example 4.

Figure 2:
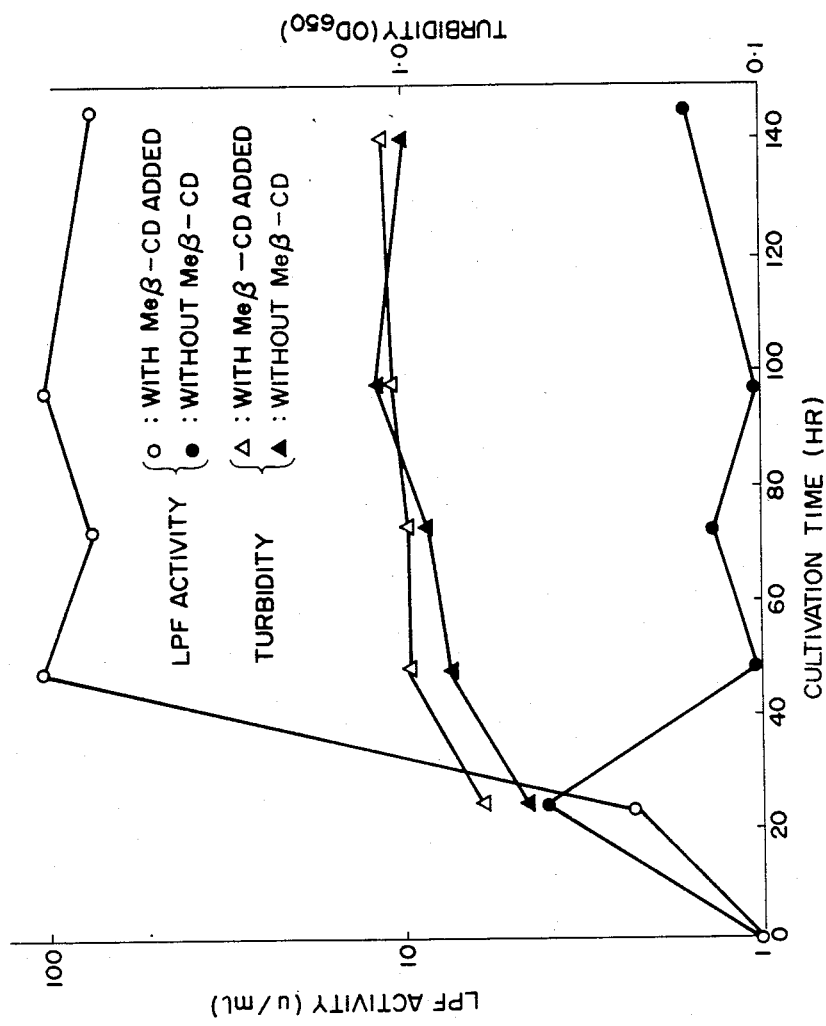
FIG. 2 is a graph to show the relationship between the cultivation time and turbidity of the culture medium or amount of LPF-HA in two cases where Meβ-CD was added to the culture medium and where not added.

It is clear from FIG. 2 that, in case where the culture time exceeds 20 hours or so, turbidities of the culture media, which indicate the absolute quantity of grown cells, do not show much difference regardless of whether Me$\beta$-CD is added or not; however, the amounts of produced LPF-HA greatly differ, showing that the presence of Me$\beta$-CD enhances the LPF productivity of Bordetella pertussis.

EXAMPLE 6

SSB medium of improved type was prepared by adding casamino acid at a ratio of 10 mg/ml and further a modified supplemental solution, which was made to contain reduced glutathione 1.5 times and ascorbic acid 20 times the standard content, at an amount of 1.0% (v/v) respectively to the base of ordinary SSB medium. Me$\beta$-CD was added to the respective portions of thus prepared SSB medium of improved type at amounts of 50, 500, 2000, and 5000 $\mu$g/ml and 200 ml of the respective portions were separately placed in Sakaguchi's flasks. Each medium was inoculated with Bordetella pertussis Tohama phase I at cell concentration of $1.5 \times 10^9$ cells/ml and cultivation was conducted at 35° C.

Figure 3:
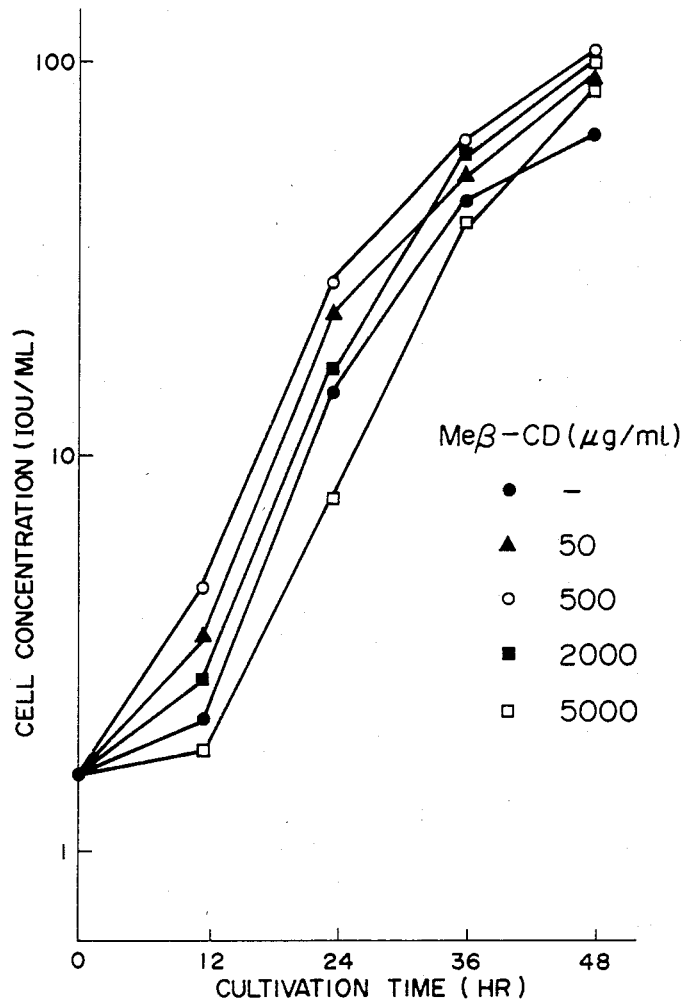
FIGS. 3 and 4 are graphs to respectively show the relationship between the cultivation time and cell concentration or amount of produced LPF-HA when *Bordetella pertussis* phase I was grown in the culture medium containing casamino acid and Meβ-CD.
Figure 4:
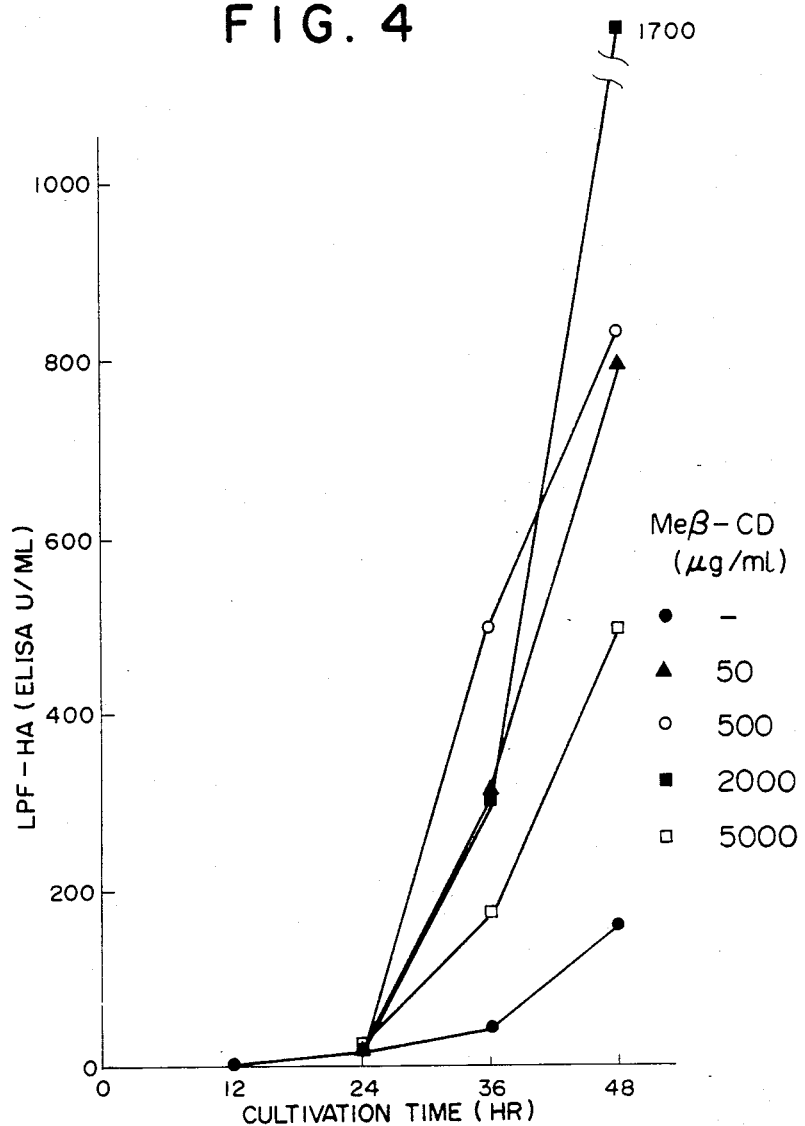

The results are shown in FIG. 3 and FIG. 4. FIG. 3 shows the relationship between the cell concentration (IOU/ml) and cultivation time, and FIG. 4 shows LPF-HA activity determined by the ELISA method as it changes with the passing of time.

It is clear from FIGS. 3 and 4 that the addition of Me$\beta$-CD to the culture medium from 50 $\mu$g/ml to 2000 $\mu$g/ml enhances both the growth of bacterial cells and the production of LPF-HA.

Incidentally, IOU is an abbreviation for International Opacity Unit and 1 IOU is equal to $10^9$ cells.

EXAMPLE 7

(1) Cultivation.

SSB medium of improved type was prepared by adding casamino acid at an amount of 10 mg/ml and Me$\beta$-CD at an amount of 2 mg/ml and further a modified supplemental solution, which was prepared in such a way as to contain glutathione of reduced type 1.5 times and ascorbic acid 20 times the standard content, at an amount of 1.0% (v/v) respectively to the base of ordinary SSB medium. Thus prepared SSB medium of improved type was inoculated with Bordetella pertussis phase I at cell concentration of $1.0 \times 10^9$ cells/ml, and placed in a 5-liter jar fermentor for cultivation. After the 48-hour cultivation was over, it was found that cell concentration was reacted about $10^{12}$ cells/ml and the amount of produced LPF-HF was determined to be 1250 U/ml according to the ELISA method. The supernatant (3.6 l) obtained by centrifuging the culture fluid at 6,000 rpm for 30 minutes was subjected to the following processes of separation and purification of LPF-HA.

(2) Separation of LPF-HA from the culture supernatant and purification thereof.

3.6 l of the supernatant (pH 8.3) obtained from the culture fluid was applied to a column (100 ml) of hydroxylapatite (manufactured by BDH Chemicals) equilibrated with 0.01M phosphate buffer (pH 8) at about 4° C. at a flow rate of 200 ml/hr. The column was washed with 0.4 l of 0.01M phosphate buffer (pH 8) and the solution passing through the column amounting to a total volume of 4 liter was adjusted to pH 6 with concentrated hydrochloric acid. This solution was applied to a column (140 ml) of hydroxylapatite equilibrated with 0.01M phosphate buffer (pH 6) at a flow rate of 100 ml/hr. The column was washed with 0.5 l of 0.01M phosphate buffer (pH 6) and washed again with 250 ml of 0.1M phosphate buffer (pH 7). The bounded protein was eluted fractionally with 0.1M phosphate buffer (pH 7) containing 0.5M sodium chloride. The obtained protein fractions were pooled (100 ml) and applied to a haptoglobin-Sepharose 4B column (30 ml) equilibrated with 0.1M buffer containing 0.5M sodium chloride. The bounded protein was eluted fractionally with 0.1M phosphate buffer (pH 7) containing 3M potassium thiocyanate and 0.5M sodium chloride. The obtained protein fractions were pooled and dialyzed against 0.1M phosphate buffer (pH 7) containing 0.5M sodium chloride to obtain 20.7 mg of LPF-HA.

This substance formed a single band in the disk electrophoresis of polyacrylamide gel (polyacrylamide concentration-7.5%, INKOH-acetic acid buffer-pX 4.3) and the mobility coincided with the known position of LPF-HA. The ELISA value of this substance was 111.1 u/$\mu$g.

What is claimed is:

1. A method of culturing microbes which belong to the genus Bordetella comprising culturing said microbes in a culture medium useful for cultivating said microbes wherein said culture medium comprises etherified cyclodextrin as an additional component.

2. The method of culturing according to claim 1, wherein said etherified cyclodextrin is methylcyclodextrin.

3. The method of culturing according to claim 2, wherein said methylcyclodextrin is hexakis(2,6-O-dimethyl)$\alpha$-cyclodextrin or heptakis(2,6-O-dimethyl)$\beta$-cyclodextrin.

4. A culture medium useful for culturing microbes belonging to the genus Bordetella, wherein said culture medium comprises as an additional component etherified cyclodextrin.

5. The culture medium according to claim 4, wherein said culture medium contains etherified cyclodextrin at a ratio of 1 to 5000 μg/ml.

6. The culture medium according to claim 5, wherein said culture medium additionally comprises casamino acids at a ratio of 0.5 to 10 mg/ml.

7. A method for producing biologically active substances comprising (1) culturing microbes belonging to the genus Bordetella in a culture medium useful for culturing said microbes, wherein said culture medium comprises as an additional component etherified cyclodextrin and (2) obtaining the biologically active substances from the culture medium, wherein said biologically active substances are selected from the group consisting of LPF-HA and F-HA.

* * * * *